United States Patent [19]

Brown et al.

[11] Patent Number: 4,933,181

[45] Date of Patent: Jun. 12, 1990

[54] SYNERGISTIC INSECTICIDAL COMPOSITIONS AND METHOD FOR USE OF SAME

[75] Inventors: Thomas M. Brown; Patricia K. Bryson, both of Clemson, S.C.

[73] Assignee: Clemson University, Clemson, S.C.

[21] Appl. No.: 280,548

[22] Filed: Jan. 17, 1989

Related U.S. Application Data

[63] Continuation of Ser. No. 943,846, Dec. 22, 1986, and a continuation of Ser. No. 555,535, Nov. 28, 1983, abandoned.

[51] Int. Cl.$^5$ .................... A01N 25/00; A01N 25/08; A01N 57/00; A61K 31/67
[52] U.S. Cl. .................... 424/405; 424/409; 514/95; 514/122; 514/132
[58] Field of Search .......... 514/95, 122, 132; 424/405, 409

[56] References Cited

U.S. PATENT DOCUMENTS 3,138,522  6/1964  Plapp et al. ................. 514/122

FOREIGN PATENT DOCUMENTS 2727479  11/1978  Fed. Rep. of Germany ...... 424/405

OTHER PUBLICATIONS

Fukuto, Chem. of Org. Insecticides 1961, Am. Rev. Entomol., pp. 318–319.
Tahori et al., Ent. Exp. App. 9(1966):99.

*Primary Examiner*—Joseph L. Schofer
*Assistant Examiner*—C. Pili-Curtis
*Attorney, Agent, or Firm*—Dority & Manning

[57] ABSTRACT

Synergistic insecticidal mixtures containing at least one primary insecticide and a synergist therefor, the synergist having the formula

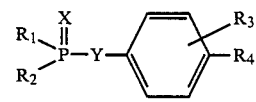

X is O or S
Y is O or S
$R_1 = R_2$ and is aryl, substituted aryl, heterocyclic, or substituted heterocyclic
$R_3$ is H or alkyl, and
$R_4$ is an electron acceptor from the phenyl group to facilitate cleavage of the P-Y bond as exemplified by $NO_2$, Cl, and $NH_2$.

Method of use of same is also disclosed and claimed.

10 Claims, No Drawings

SYNERGISTIC INSECTICIDAL COMPOSITIONS AND METHOD FOR USE OF SAME

This is a continuation of application Ser. Nos. 943,846 and 555,535, filed Dec. 22, 1986 and Nov. 28, 1983 now abandoned.

BACKGROUND OF THE INVENTION

The present invention relates to synergistic insecticidal compositions and the method of use of same such that an insect which has developed resistance to certain insecticides can be controlled and/or annihilated with the particular insecticide.

In the development of an insecticide to be used for the control and annihilation of flies, mosquitos, milkweed bugs, tobacco budworms, rust-red flour beetles and the like, a number of factors come into play which must be considered prior to commerical use of the particular insecticide. First of course the insecticide must have adequate efficacy for the particular insect such that the effective lethal dosage of the insecticide is practical, i.e., that the effective ingredient of the overall insecticide composition is at an adequately low level to ensure economical justification and that no adverse side effects are created thereby. Insofar as side effects are concerned, since the insecticidal composition will be generally sprayed or otherwise admitted to the atmosphere, it is imperative that the effective constituent of composition not be toxic to humans, pets, or wildlife and the like above and beyond the targeted population. As to toxicity, while a number of insecticides are quite lethal to the targeted population, many also possess sufficient toxicity that they cannot be used for fear of immediate or delayed toxic reaction in humans, pets, or wildlife and the like. It has been determined for example that certain insecticides create delayed neurotoxic reactions in hens. In fact, a generally accepted test as to toxicity is to determine whether there is a delayed neurotoxicity in hens.

As certain insecticides have been continuously used commercially for the control and elimination of insects, the insects have developed a resistive mechanism to the particular insecticide. In general the insecticidal activity has entailed the inhibition of activity within the insect, such as for example, the inhibition of acetyl cholinesterase enzymes along the nerve cord. Resistance to the insecticide has, however, come about by virtue of enzymatic activity such as carboxyl esterase enzymes which chemically neutralize the insecticides against inhibition of the acetyl cholinesterase. Depending upon the particular insecticide being utilized the carboxyl esterase enzyme may chemically tie up, or chemically degrade one or more molecules of insecticide per molecule of the exterase enzyme. Consequently such interaction renders the insect resistant to the particular insecticide. Likewise other interactions may occur between insecticides and proteins or other enzymes within the insect.

In order to overcome the resistance to particular insecticides, others have therefore discovered particular compounds which, when added to the insecticide, will act as a synergist therewith and overcome to some degree the resistive mechanism. The insecticide is then returned to an efficacious posture. Arend et al have disclosed a number of such synergists as set forth in Offenlegungsschrift 27 27 479. The Arend et al synergists cover a wide range of compounds, including certain organophosphinates, though different from the phosphinates of the present invention. Arend et al further set forth the efficacy of a large number of insecticides per se as well as the efficacy of the insecticides in admixture with the disclosed synergists. Further, Fukuto in the "Chemistry of Organic Insecticides," 1961 *Ann. Rev. Entomol.*, 6:313 discusses the efficacy and toxicity of para-nitrophenyl dialkylphosphinates with the insecticidal efficacy of the compounds being directed to house flies. Likewise, Tahori et al in "Anticholinesterase Activity (In the Mediterranean Fruit Fly) and Mouse Toxicity of Some New Organophosphorous Compounds", *Ent. exp. & appl.* 9(1966):99 disclose certain organophosphinate as insecticidal. Though Fukuto and Tahori et al discusses the insecticidal properties of certain organophosphinates, and though Arend et al. disclose among many other candidates several organophosphinates as synergists for insecticides, there is no teaching or suggestion therein of the use of the particular genus of organophosphinates according to teachings of the present invention as insecticidal synergists.

Summary of the Invention

It is an object of the present invention to provide an improved insecticidal composition that is efficacious as to the targeted population while low in toxicity.

Yet another object of the present invention is to provide an improved insecticidal composition that overcomes resistance of the insect to the primary insecticide being utilized.

Still further another object of the present invention is to provide an improved insecticidal composition that includes a particular group of organophosphinates as synergists.

Yet a further object of the present invention is to provide a method for overcoming the resistance of an insect to a particular insecticide.

Another object of the present invention is to provide a method for overcoming enzymatic resistance to the efficacy of an insecticide by the addition of a particular organophosphinate synergist in admixture with the insecticide.

Generally speaking the improved insecticidal composition according to the present invention comprises a primary insecticide and a synergistic amount of an organophosphinate having the formula

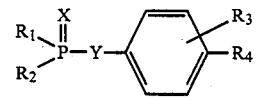

X is O or S
Y is O or S
$R_1 = R_2$ and is aryl, substituted aryl, heterocylic, or substituted heterocyclic
$R_3$ is H or alkyl, and
$R_4$ is an electron acceptor from the phenyl group to facilitate cleavage of the P-Y bond as exemplified by $NO_2$, Cl, and $NH_2$ More specifically, the improved insecticidal compositions according to teachings of the present invention include a carrier, a predetermined amount of a primary insecticide, and a synergistic quantity of preferably a 4-nitrophenyl bis substituted organophosphinate where the bis substituents are aryl groups, substituted aryl groups, heterocyclic groups, and substituted heterocyclic groups. Most preferably the organophosphinate synergist is a bis substituted organophosphinate as defined herein where the sustituent is a phenyl group or a 2-thienyl group.

The method according to teachings of the present invention for overcoming insect resistance to a particular primary insecticide comprises the steps of adding to the primary insecticide a compound having the general formula

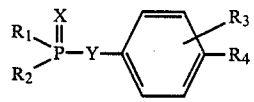

X is O or S
Y is O or S
$R_1 = R_2$ and is aryl, substituted aryl, heterocyclic, or substituted heterocyclic
$R_3$ is H or alkyl, and
$R_4$ is an electron acceptor from the phenyl group to faciliate cleavage of the P-Y bond as exemplified by $NO_2$, Cl, and $NH_2$, the organophosphinate being added in a synergistic amount, and subjecting the insect to the admixture whereby the synergist neutralizes the resistance mechanism of the insect against the efficacy of the insecticide.

In a most preferred embodiment, the method according to the present invention comprises the steps of adding a synergistic amount of a 4-nitrophenyl bis substituted organophosphinate to the primary insecticide wherein the substituents of the organophosphinate are aryl groups, substituted aryl groups, heterocyclic groups, or substituted heterocyclic groups.

DESCRIPTION OF THE PREFERRED EMBODIMENTS

The improved insecticidal compositions according to teachings of the present invention comprise an efficacious amount of a primary insecticide, a carrier for the insecticide, an organophosphinate synergist that is stable, non-neurotoxic, and which will neutralize by phosphinylation certain enzymes within the body of the insect which otherwise would neutralize the efficacy of the primary insecticide. produced is brought into contact with the target insect population in a predetermined quantity adequate to achieve a predetermined degree of insect mortality. Normally the insecticidal composition and synergist are dissolved in the carrier and the carrier is then emulsified in water. The emulsion is then generally sprayed over extended areas where the target insect population resides in an effort to control and/or annihilate same, though insecticidal compositions according to teachings of the present invention may otherwise be applied, such as oil formulations, in which the carrier, insecticide and synergist are dissolved and/or emulsified; dust formulation in which the insecticide and synergist are deposited onto a fine particle compound such as talc; and wettable powders in which a dust powder type composition includes a surfactant to permit suspension in water.

Insofar as the insecticidal compositions of the present invention are concerned, the primary insecticide may be any of the known insecticides or mixtures of insecticides, which when brought into contact and ingested by the insect, will inhibit acetylcholinesterase enzymatic activity or otherwise inhibit vital physiological functions and thus lead to expiration of the insect. Such primary insecticides include without limitation carbaryl, methyl parathion, pirimiphos methyl; lindane; malathion; and permethrin. The amount of primary insecticide present in an overall composition will vary, depending upon the target insect population to which it is to be directed, as well as the particular synergist that is used in conjunction therewith. Clearly one skilled in the art, once knowledgable, of the disclosure of the present subject matter can, without undue experimentation, determine an efficacious amount of primary insecticide that needs to be present in a particular overall composition in order to achieve the desired degree of mortality. Furthermore, as may be seen hereinafter, relative ratios of primary insecticide to synergist may vary considerably as set forth.

Carriers for the effective insecticidal ingredients according to teachings of the present invention may be any conventional carrier system that is commonly used for such purpose and which is suitable for the particular type application to be made. Exemplary of conventional carrier systems are ethanol, acetone, and oils as exemplified by Shellflex 210 oil, a mineral oil based product manufactured by Shell Chemical Company, or the like. Preferably, the primary insecticide and synergist according to the present invention are dissolved in the carrier after which the carrier is formulated into an overall composition for spray or other type application as desired. As mentioned above, however, other type carriers may be employed such as the solid diluents. The overall insecticide composition, in addition to the carrier oil having the insecticide and synergist dissolved therein would normally include a particular emulsifying agent that is preferably matched to the particular carrier, the insecticide and the synergist, and water. Matching of the emulsifying agent to the other compounds assists in achieving proper emulsification of the insecticide-synergist containing carrier oil in the water for spray or other type application. Such is particularly important since the farmer, gardener, housewife or other user generally prepares the oil in water emulsion. Other conventional additives may likewise be present.

Particular organophosphinates that are synergists for the insecticides according to the present invention include those organophosphinates that are defined by the formula

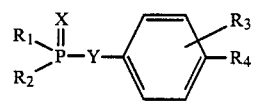

X is O or S
Y is O or S
$R_1 = R_2$ and is aryl, substituted aryl, heterocyclic, or substituted heterocyclic
$R_3$ is H or alkyl, and
$R_4$ is an electron acceptor from the phenyl group to facilitate cleavage of the P-Y bond as exemplified by $NO_2$, Cl, and $NH_2$ Examples of suitable substituents for the generic formula include without limitatin $R_1$ $R_1$ groups of

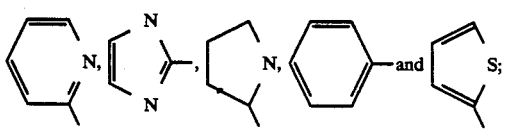

X groups of S and O; Y groups of O or S; $R_3$ groups of H and $CH_3$ and $R_4$ groups of $NO_2$, Cl, $NH_2$. Most preferably the organophosphinates according to the present invention have the formula

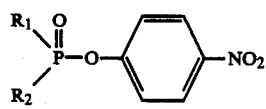

where $R_1$ and $R_2$ are phenyl or 2-thienyl.

In formulating a particular synergistic insecticidal formulate according to the present invention, particular synergists as described may be included alone or in combination with other known synergists in like fashion as mentioned above with respect to the primary insecticides.

Particular phosphinates that serve as synergistic agents according to the present invention do not exhibit any delayed neurotoxicity characteristics. Confirmation of same is set forth in an article in the *Journal of Neurochemistry*, Vol. 23, Pages 785–789 by M. K. Johnson. Johnson concludes in *Reviews in Biochemical Toxicology*, vol. 4, pp. 141–212 that in order for an organophosphorous compound to create delayed neurotoxicity, it is necessary for two oxygen phosphorus linkages to be present in addition to that of the leaving group. Organophosphinates actually evaluated by Johnson do not include any of those according to teachings of the present invention but do have direct carbon-phosphorus linkages in the $R_1$ and $R_2$ positions in similar fashion to the bis substituted phosphinates as described above. Preferred organophosphinate synergists of the present invention are 4-nitrophenyl diphenylphosphinate and 4-nitrophenyl bis (2-thienyl) phosphinate, both of which exhibit enhanced results when utilized on insects in conjunction with a primary insecticide where the carboxyl esterase mechanism is present, which if not blocked by the synergist catalyzes degradation of the insecticide.

In order to more fully understand the present invention, the following examples are set forth.

EXAMPLES 1-22

Tests were run on *Tribolium castaneum* adults (rust-red flour beetle) to determine the efficacy of phosphinates according to teachings of the present invention thereon. In each of the examples, the product or admixture being tested was dissolved in Shellflex 210 and chloroform and added to Whatman 1 filter paper after which chloroform was allowed to evaporate. Thereafter the beetles were confined for 24 hours at 25° C. on the impregnated Whatman 1 filter paper with the percentage of mortality of the beetles being determined after the 24 hour period. A plurality of replicates of 40 beetles each were tested. Particular compounds tested per se, and admixtures of insecticide and synergist are set forth in Table I along with the dosages utilized and the percent of mortality determined.

TABLE I
SYNERGISM OF INSECTICIDES BY ORGANOPHOSPHINATES IN *TRIBOLIUM CASTANEUM* ADULTS (RUST-RED FLOUR BEETLE)

| Example No. | Treatment | Dose % in oil | % Mortality |
|---|---|---|---|
| 1 | Shellflex 210 oil (carrier) | — | 0 |
| 2 | 4-nitrophenyl diphenylphosphinate | 2 | 0 |
| 3 | 4-nitrophenyl bis (2-thienyl) phosphinate | 2 | 0 |
| 4 | carbaryl | 2 | 2 |
| | carbaryl admix: | | |
| 5 | 4-nitrophenyl diphenylphosphinate | 2 | 15 |
| 6 | 4-nitrophenyl bis (2-thienyl) phosphinate | 2 | 13 |
| 7 | methyl parathion | 0.005 | 28 |
| | methyl parathion admix: | | |
| 8 | 4-nitrophenyl diphenylphosphinate | 0.005 | 59 |
| 9 | 4-nitrophenyl bis (2-thienyl) phosphinate | 0.005 | 33 |
| 10 | pirimiphos methyl | 0.05 | 34 |
| | pirimiphos methyl admix: | | |
| 11 | 4-nitrophenyl diphenylphosphinate | 0.05 | 31 |
| 12 | 4-nitrophenyl bis (2-thienyl) phosphinate | 0.05 | 53 |
| 13 | permethrin | 0.5 | 22 |
| | permethrin admix: | | |
| 14 | 4-nitrophenyl diphenylphosphinate | 0.5 | 24 |
| 15 | 4-nitrophenyl bis (2-thienyl) phosphinate | 0.5 | 45 |
| 16 | lindane | 0.25 | 13 |
| | lindane admix: | | |
| 17 | 4-nitrophenyl diphenylphosphinate | 0.25 | 20 |
| 18 | malathion | 0.5 | 22 |
| | malathion admix: | | |
| 19 | 4-nitrophenyl diphenylphosphinate | 0.5 | 100 |
| 20 | 4-nitrophenyl diphenylphosphinate | 0.25 | 100 |
| 21 | 4-nitrophenyl bis (2-thienyl) phosphinate | 0.5 | 100 |
| 22 | 4-nitrophenyl bis (2-thienyl) phosphinate | 0.25 | 100 |

As can be seen from the results set forth in Table I, the carrier of course possesses absolutely no insecticidal properties, as expected. In Examples 2 and 3, however, the preferred candidates of the particular organophosphinates according to the present invention at a dosage rate of 2% in the mineral oil product, yielded no mortality. When, however, the 4-nitrophenyl diphenylphosphinate, (Example 5) and 4-nitrophenyl bis (2-thienyl) phosphinate (Example 6) was utilized in conjunction with carbaryl insecticide, a significant increase in mortality was noted above that of the carbaryl insecticide alone (Example 4). Likewise with malathion, methyl parathion, pirimiphos methyl and permethrin similar results were evident, i.e. the admixture of the primary insecticide and either the 4-nitrophenyl diphenylphosphinate or the 4-nitrophenyl bis (2-thienyl) phosphinate yielded a higher percentage of mortality of the beetles than when the insecticide was utilized alone. Table I therefore clearly demonstrates the synergistic effects achieved by utilizing the primary insecticide in conjunction with the synergist organophosphinate according to the present invention.

EXAMPLES 23-26

Examples 23-26 represent further tests of the synergistic activity of 4-nitrophenyl bis (2-thienyl) phosphinate for *Heliothis virescens* (tobacco budworm). The particular effective ingredients were dissolved in acetone and applied by way of an Isco Model M microapplicator to the dorsal thoraces of tobacco budworm larva weighing 35 mg. Mortality was then assessed after 48 hours as an inability for the larvae to translocate when probed. The particular examples and results for same are set forth in Table II.

As can be seen from the results set forth in Table I, the carrier of course possesses absolutely no insecticidal properties, as expected. In Examples 2 and 3, however, the preferred candidates of the particular organophosphinates according to the present invention at a dosage rate of 2% in the mineral oil product, yielded no mortality. When, however, the 4-nitrophenyl diphenylphosphinate, (Example 5) and 4-nitrophenyl bis (2-thienyl) phosphinate (Example 6) was utilized in conjunction with carbaryl insecticide, a significant increase in mortality was noted above that of the carbaryl insecticide alone (Example 4). Likewise with malathion, methyl parathion, pirimiphos methyl and permethrin similar results were evident, i.e. the admixture of the primary insecticide and either the 4-nitrophenyl diphenylphosphinate or the 4-nitrophenyl bis (2-thienyl) phosphinate yielded a higher percentage of mortality of the beetles than when the insecticide was utilized alone. Table I therefore clearly demonstrates the synergistic effects achieved by utilizing the primary insecticide in conjunction with the synergist organophosphinate according to the present invention.

EXAMPLES 23-26

Examples 23-26 respresent further tests of the synergistic activity of 4-nitrophenyl bis (2-thienyl) phosphinate for Heliothis virescens (tobacco budworm). The particular effective ingredients were dissolved in acetone and applied by way of an Isco Model M microapplicator to the dorsal thoraces of tobacco budworm larva weighing 35 mg. Mortality was then assessed after 48 hours as an inability for the larvae to translocate when probed. The particular examples and results for same are set forth in Table II.

TABLE II

SYNERGISM OF METHYL PARATHION BY 4-NITROPHENYL BIS (2-THIENYL PHOSPHINATE) IN HELIOTHIS VIRESCENS

| Example No. | Treatment | Dose, μg larva | Mortality |
|---|---|---|---|
| 23 | 4-nitrophenyl bis (2-thienyl) phosphinate | 33 | 0/10 |
| 24 | methyl parathion | 17.5 | 2/10 |
|  | methyl parathion admix: |  |  |
| 25 | 4-nitrophenyl bis (2-thienyl) phosphinate | 33 | 3/10 |
| 26 | acetone | 1000 | 0/10 |

As can be seen from Table II, though 4-nitrophenyl bis (2-thienyl) phosphinate at a dosage of 33 micro grams per larva showed no mortality, a like amount of same, when admixed with 17.5 micro grams of methyl parathion, yielded a mortality rate increase of 50% over a dosage rate of 17.5 micro grams per larva of methyl parathion alone. Such indicates synergistic activity of the 4-nitrophenyl bis (2-thienyl) phosphinate.

EXAMPLES 27-31

In examples 27-31 efficacy of the synergistic action of the 4-nitrophenyl bis (2-thienyl) phosphinate was likewise tested in conjunction with malathion for Oncopeltus fasciatus (large milkweed bug). The particular coumpounds being tested were dissolved in acetone and applied by way of the Isco microapplicator to the dorsal thoraces of nymphs weighing 4.5 mg. Mortality was tested as the inability of a nymph to translocate when probed after 48 hours. Table III lists the particular compounds being tested, the dosage level and the mortality.

TABLE III

SYNERGISM BY 4-NITROPHENYL BIS (2-THIENYL) PHOSPHINATE IN ONCOPELTUS FASCIATUS

| Example No. | Treatment | Dose, μg/nymph | Mortality |
|---|---|---|---|
| 27 | malathion | 0.22 | 2/10 |
| 29 | 4-nitrophenyl bis (2-thienyl) phosphinate | 0.11 | 0/10 |
|  | malathion admix: |  |  |
| 30 | 4-nitrophenyl bis (2-thienyl) phosphinate | 0.11 | 9/10 |
| 31 | acetone | 1000 | 3/10 |

As can be seen from Table III again, the 4-nitrophenyl bis (2-thienyl) phosphinate exhibited synergism when admixed with malation. In fact as seen in Example 28 when malathion was applied at a dosage rate of 0.22 micro grams per nymph, a mortality of 2 out of 10 was observed, whereas when ½ the dosage level of malathion was admixed with a like amount of 4-nitrophenyl bis (2-thienyl) phosphinate mortality increased to 9 out of 10. When the 4-nitrophenyl bis (2-thienyl) phosphinate was utilized alone, no insecticidal activity was evident.

As can be seen from Examples 1-31, the particular bis substituted organophosphinates according to the present invention in all instances demonstrated synergism with the primary insecticide. As can be seen from the examples, the relative dosage rates of synergist to primary insecticide ranged from 0.5:1 to about 5:1 parts by weight. As mentioned above, however, depending upon the particular efficacy of the specific primary insecticide and the actual blocking mechanism, the ratio of synergist to insecticide may vary considerably, falling in a range of from about 0.25 parts synergist to 1 part insecticide to about 10 parts synergist to 1 part insecticide. Such likewise takes into consideration economical considerations as to the particular insecticide and synergist being utilized.

Having described the present invention in detail, it is obvious that one skilled in the art will be able to make variations and modifications thereto without departing from the scope of the invention. Accordingly, the scope of the present invention should be determined only by the claims appended hereto.

That which is claimed is:

1. A synergistic insecticidal mixture for inhibiting acetylcholinesterase enzymatic activity comprising a primary insecticide and a synergist therefor, said synergist comprising a compound having the formula:

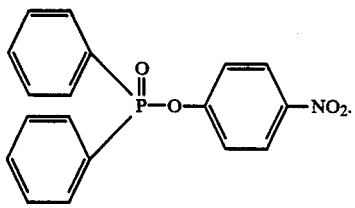

2. A synergistic insecticidal mixture for inhibiting acetylcholinesterase enzymatic activity comprising a primary insecticide and a synergist therefor, said synergist comprising a compound having the formula:

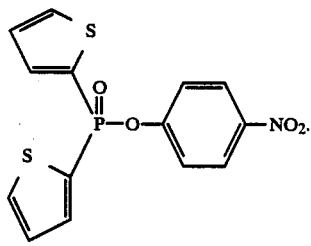

3. A synergistic insecticidal mixture as defined in claim 2, wherein said primary insecticide is a member selected from the group consisting of malathion, methyl parathion, carbaryl, pirimiphose, permethrin and lindane.

4. A synergistic insecticidal mixture as defined in claim 2, wherein the mixture is dissolved in a carrier therefor.

5. A synergistic insecticidal mixture as defined in claim 2, said mixture being dissolved in a carrier therefor, an emulsifying agent and water.

6. A synergistic insecticidal mixture as defined in claim 1 wherein the primary insecticide is a member selected from the group consisting of malathion, methyl parathion, carbaryl, pirimiphos, permethrin, and lindane.

7. A synergistic insecticide mixture as defined in claim 1 wherein the mixture is dissolved in a carrier therefor.

8. A synergistic insecticide composition comprising a mixture as defined in claim 1, said mixture being dissolved in a carrier therefor, an emulsifying agent and water.

9. A synergistic insecticide mixture for inhibiting acetylcholinesterase enzymatic activity comprising malathion and 4 nitrophenyl bis (2-thienyl) phosphinate, said phosphinate and malathion being present in a ratio in a range of from about 0.25 to 1.0 to about 10.0 to 1.0.

10. A synergistic insecticidal mixture for inhibiting acetylcholinesterase enzymatic activity comprising malathion and 4-nitrophenyl diphenylphosphinate, said phosphinate and said malathion being present in a ratio in a range of from about 0.25 to 1.0 to about 10.0 to 1.0.

* * * * *